(12) United States Patent
Heidenreich et al.

(10) Patent No.: US 7,729,929 B2
(45) Date of Patent: Jun. 1, 2010

(54) METHOD AND APPARATUS FOR DELIVERY OF MEDICAL ITEMS ON AN ELECTRONIC PRESCRIPTION

(75) Inventors: Georg Heidenreich, Erlangen (DE); Sultan Haider, Erlangen (DE)

(73) Assignee: Siemens Aktiengesellschaft, Munich (DE)

( * ) Notice: Subject to any disclaimer, the term of this patent is extended or adjusted under 35 U.S.C. 154(b) by 0 days.

(21) Appl. No.: 11/580,325

(22) Filed: Oct. 13, 2006

(65) Prior Publication Data

US 2008/0091468 A1   Apr. 17, 2008

(51) Int. Cl.
*G06F 19/00* (2006.01)
(52) U.S. Cl. .................. 705/3; 705/2; 600/300
(58) Field of Classification Search .............. 705/2–3
See application file for complete search history.

(56) References Cited

U.S. PATENT DOCUMENTS

| | | | |
|---|---|---|---|
| 5,301,105 A * | 4/1994 | Cummings, Jr. ............... | 705/2 |
| 5,845,255 A * | 12/1998 | Mayaud ......................... | 705/3 |
| 6,315,720 B1 * | 11/2001 | Williams et al. ............. | 600/300 |
| 2002/0029223 A1 * | 3/2002 | Rice et al. .................. | 707/104.1 |
| 2002/0042724 A1 * | 4/2002 | Victor ........................... | 705/2 |
| 2003/0130875 A1 * | 7/2003 | Hawash et al. ................. | 705/3 |
| 2003/0158469 A1 * | 8/2003 | Elsayed et al. ............. | 600/300 |
| 2003/0236681 A1 * | 12/2003 | Ninomiya et al. .............. | 705/2 |
| 2005/0010442 A1 * | 1/2005 | Kragh ........................... | 705/2 |
| 2006/0261145 A1 * | 11/2006 | Robertson et al. ........... | 235/375 |

* cited by examiner

*Primary Examiner*—C. Luke Gilligan
*Assistant Examiner*—Dilek B Cobanoglu
(74) *Attorney, Agent, or Firm*—Schiff Hardin LLP

(57) ABSTRACT

A method for dispensing medical items designated in a prescription, such as an electronic prescription, including providing the electronic prescription to a server, and the server providing the electronic prescription to a pharmacy or other agent that fills the prescription and provides the medical items to the patient. A consent statement is provided by the patient for permission to the pharmacy to receive and fill the prescription and for permission to the server to receive and forward the prescription. Secure communications are provided for key communications to establish trust of identity of the parties and entities.

5 Claims, 4 Drawing Sheets

METHOD AND APPARATUS FOR DELIVERY OF MEDICAL ITEMS ON AN ELECTRONIC PRESCRIPTION

BACKGROUND OF THE INVENTION

1. Field of the Invention

The present invention relates generally to a method and system for providing medical items on an electronic prescription to a patient.

2. Description of the Related Art

A person needing medicine or medical items, such as medical equipment or the like, can obtain the medicines and medical equipment from a pharmacy or other medical supply entity. Dispensing of medicines and medical items is in many instances controlled so that the medical items and medicines may only be dispensed by prescription. It is also possible that the prescription is required for an insurer or medical assistance agency, such as Medicaid, to pay or assist in payment for the medical item. Electronic prescriptions, also referred to as e-prescriptions, are electronic versions of the paper prescriptions that are commonly issued by doctors and other medical professionals.

Patients who need medicine and medical aids are, in many cases, not able to personally obtain the prescription for the medicine or medical aid. Patients will not or can not, in some cases, go to a pharmacy to purchase the prescribed items to bring the medicine or medical aid to their home or care setting.

In such cases, an agent, such as a relative, spouse or friend may act on behalf of the patient and go to the issuer of the prescription to pick up the prescription, then to the pharmacy to have the prescription filled and obtain the medicine or medical aid. The agent pays for the medicine or medical aid and brings it to the patient.

SUMMARY OF THE INVENTION

The present invention provides a method and system for providing medical items to a patient, wherein a prescription is written for the patient by a medical care giver. The prescription is presented to a server or other computer system and the server or computer system communicates the prescription to a pharmacy or other agent for supplying the medical items identified on the prescription. The pharmacy or other agent supplies the medical items, such as medicine, medical devices, and the like, to the patient either by delivery, via the mail, or otherwise. The patient provides a consent statement permitting the pharmacy to receive the e-prescription and to dispense the medical items to the patient. The patient may provide the consent statement to the pharmacy or to the server. The consent statement may be a general consent or specific to a particular prescription.

DETAILED DESCRIPTION OF THE PREFERRED EMBODIMENTS

The present invention provides a method and system for providing medical needs identified in a prescription, such as an electronic prescription, to the patient. A patient consent statement, preferably in electronic form, is provided to a pharmacy to permit the pharmacy to act as an agent of the patient. The patient consent form instructs the pharmacy to dispense, deliver and bill for items prescribed for the patient without the need for any further actions by the patient. The patient consent statement may provide either that the such actions are taken per prescription or each time a prescription is presented by the patient. The per prescription arrangement requires an explicit patient confirmation of the instruction, such as a confirmation transmitted as an electronic document, via voice, via telephone, via email, or by other like means. The consent statement is owned by the pharmacy, in other words is stored at the pharmacy such as on the pharmacy computers.

Figure 1:
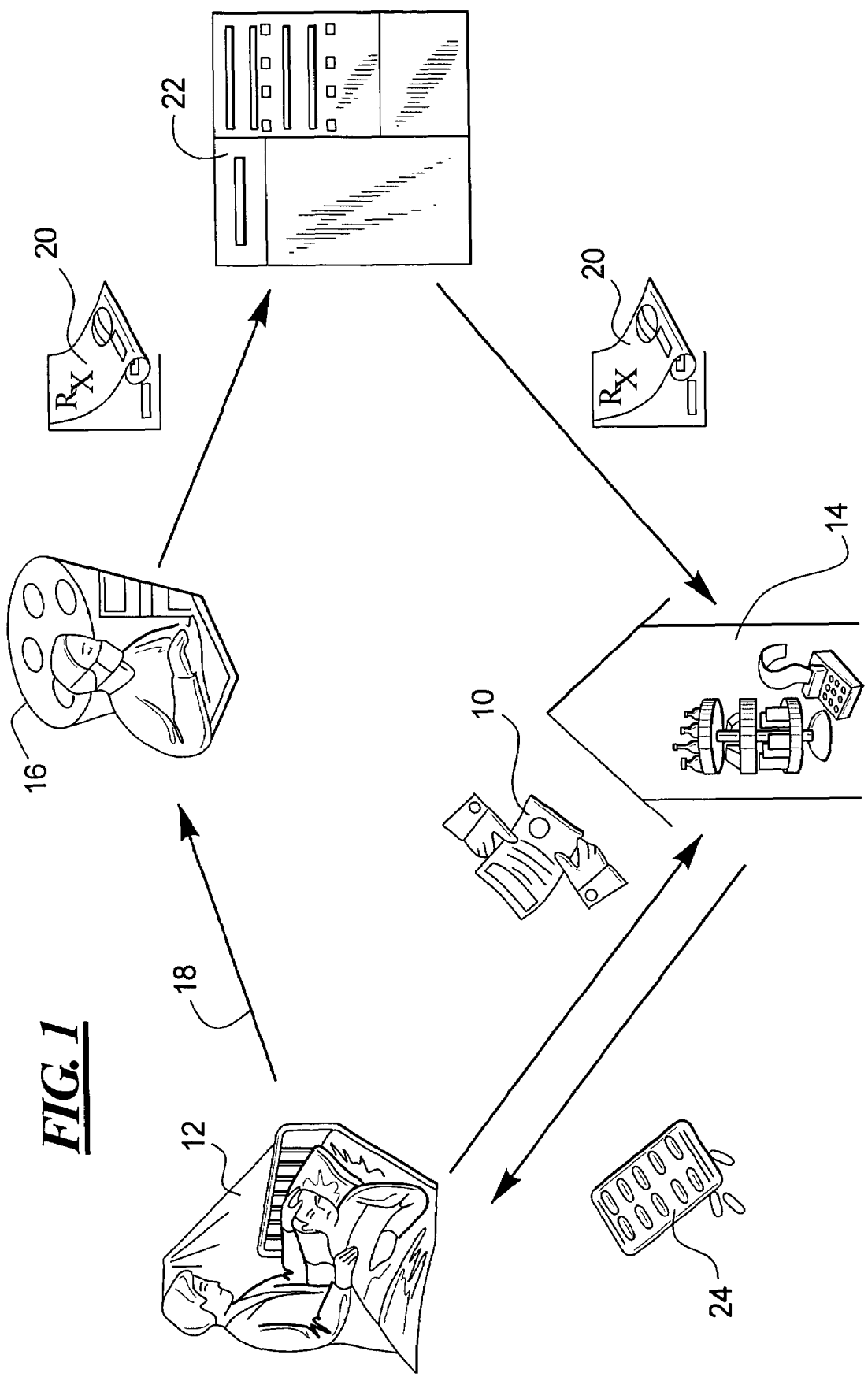
FIG. 1 is a schematic diagram of a first embodiment of the present method and system according to the principles of the present invention.

With reference to FIG. 1, a patient consent statement 10 is provided from a patient 12 to a pharmacy 14. The consent statement 10 is, in one embodiment, stored at the pharmacy 14 that is named as an agent in the consent statement. The consent 10 is in this variation a general consent. The patient 12 is seen by a medical professional 16, such as a doctor, dentist, physician's assistant, nurse, nurse's assistant, psychiatrist, or the like, as indicated at 18. The medical professional 16 prepares a prescription 20, here an electronic prescription, or e-prescription. It is not necessary in every case that the medical professional see the patient, such as where the patient is seeking a refill of a prescription or another in a continuing series of treatments.

The prescription 20 is provided to a server 22. The server 22, or other computer system, handles the prescription 20, including storing, posting, sending, or allowing access to the prescription. The prescription 20 is provided to the pharmacy 14 by the server 22. The pharmacy 14, having both the consent statement 10 of the patient 12 and the prescription 20 for that patient 12, provides the medication, medical appliance, or other item or items 24 identified on the prescription 20. The pharmacy 14 may be a single pharmacy or may be several pharmacies, a company operating several pharmacies, or one or more agents that act as the pharmacy. The pharmacy or agent 14 reads the e-prescriptions 20, controls delivery of the medicine or medical items 24, and bills for the medicine or medical items identified in the e-prescription 20.

The delivery of the medical items designated in the prescription may be by personal delivery to the patient or the residence of the patient, by courier delivery, by mail, by parcel service delivery, and the like. Delivery within the context of the present invention may also include providing the medical items or medicine directly to the patient, or to a representative of the patient, such as a spouse, parent, relative, guardian, or the like. Delivery here refers to providing the medical item or items and can include providing the medical device or medicine directly to the patient at the pharmacy, such as at a pick-up window, drive-through window, or inside the pharmacy.

Within the scope of this invention, the server 22 can be any computer device or network connected computer device, including a computer device connected to the Internet, an internal network or intranet, a wide area network, local area network, or other computer system or network. The pharmacy according to the present invention may be a pharmacy, a medical equipment or medical device company, a mail order company, a service for supplying medicine or other supplies, equipment, devices or other medical items that may be designated in a prescription.

The consent statement of a preferred embodiment is an electronic document, but it is foreseeable that the consent statement may take some other form, such as a response to questions at a secure web interface, an authorization code, vocal authorization such as authenticated by voice print or other means, or even a paper document. Other forms of the consent statements are also possible.

Alternatively to the pharmacy storing the consent statement, the patient consent statement 10 is stored by an application, for example as software application which generates electronic prescriptions, along with the electronic prescription.

The human actors involved in the process include the patient 12 who is to receive the medical items 24 identified in the e-prescription 20 and the medical professional 16 that issues the e-prescription 20. Other actors may be electronic or software actors or may include human actors.

The illustration of FIG. 1 is referred to as a "pull" variation, where the agent or pharmacy 14 keeps the patient consent 10. The agent or pharmacy 14 also keeps the data that enables the agent to perform the complete dispensing protocol. This protocol includes authentication of the pharmacy and the patient, identification of the e-prescription, and dispensing the items prescribed. The information on the server 22 is not modified in the "pull" variation.

From time to time, or after a notification from the patient 12 or from the medical personnel 16 who authored the e-prescription, the agent or pharmacy 14 polls the server 22 for pending e-prescriptions that match patients 12 mentioned in respective consent statements 10, for example that the agent 14 has in its possession.

Mutual trust between the parties in the "pull" variation is established for security reasons. The patient 12 has to trust the pharmacy 14 so that the patient has reason to believe that the pharmacy 14 will do what it has agreed to do, and so that the patient can rely on fast and correct delivery and billing. The agent or pharmacy 14 must trust the patient 12 so that the pharmacy knows, or at least has a plausible belief, that the patient 12 is entitled to receive the medical items 24 identified in the e-prescription 20 and that the items 24 will be paid for by someone, either the patient 12 or another entity (insurance, Medicare, etc.). The pharmacy 14 must trust the server 22 so that the pharmacy knows that the e-prescription server is entitled to manage this e-prescription 20. The server 22 must also trust the pharmacy 14 to be sure that the pharmacy will quickly and honestly send the correct items 24 to the correct patient 12.

Secure communications, including communications using encryption, assist in establishing the trust between the parties and entities that enables the present method to be used successfully. The encryption or other communication may use various known techniques. This establishes the identity of the communicating parties and entities, providing trust necessary for fraud prevention.

Figure 2:
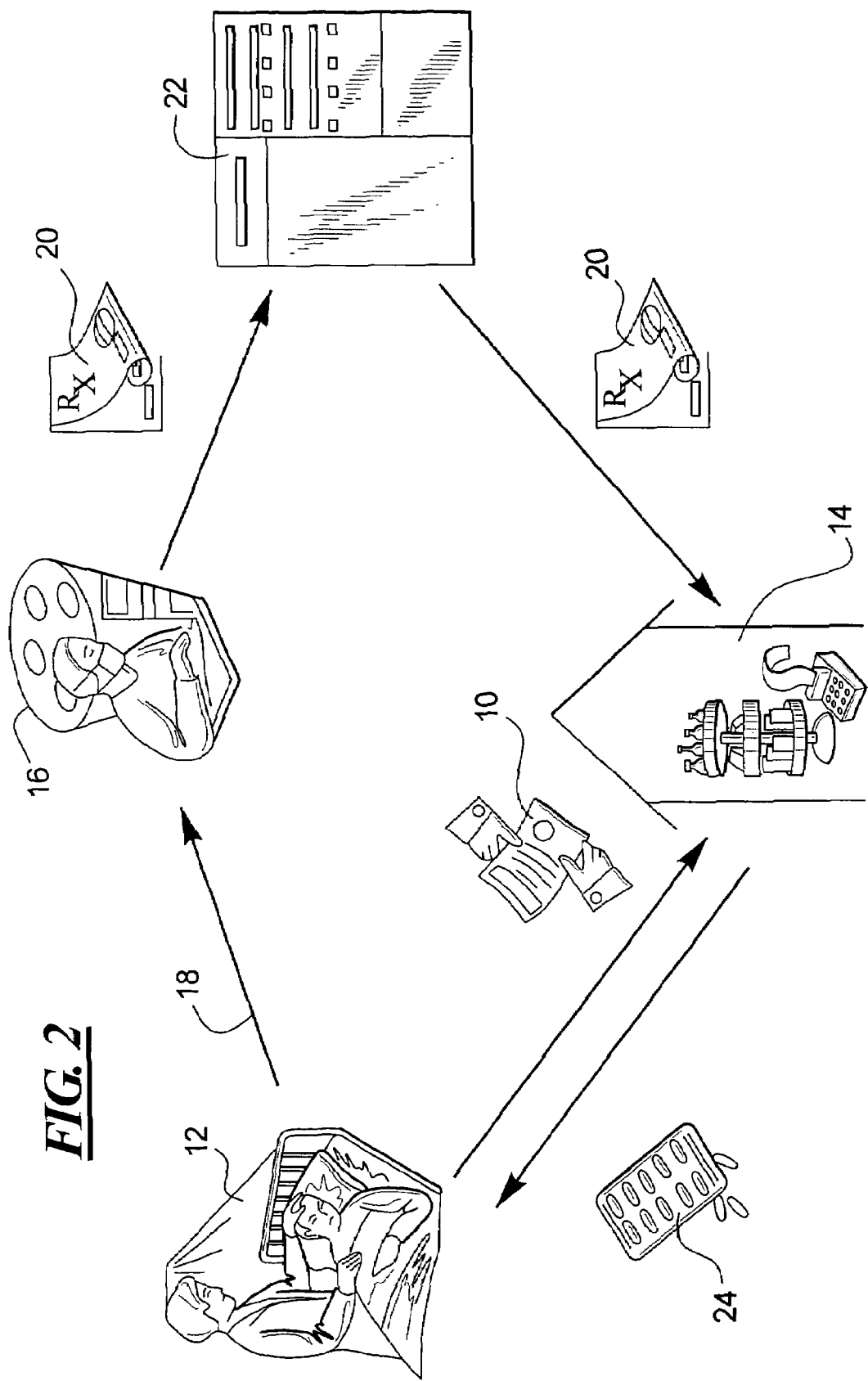
FIG. 2 is a schematic diagram of a second embodiment of the present method and system.

Instead of the general consent variation shown in FIG. 1, another version of the "pull" process provides for dispensing the medical items 24 each time the e-prescription is submitted to a patient, as shown in FIG. 2. In this case, the patient 12 first makes contact with the medical professional 16 as shown at 18, the medical professional 16 prepares the e-prescription 20 that is then stored on the server 22, and then the patient 12 provides the consent statement 10 to the pharmacy 14. The pharmacy 14 obtains the e-prescription 20 from the server 22, fills the prescription and forwards the medical items 24 to the patient 12. This per-case consent variation of FIG. 2 differs from the general consent case shown in FIG. 1, because the patient 12 has not provided a general consent 10 to the pharmacy 14 prior to the prescription 20 being prepared, whereas in the general consent case, the consent 10 is provided to the pharmacy in advance of the e-prescription being prepared.

The per-case consent may be a consent 10 only to dispense the medical items 24 for the e-prescription in this one case, or the consent 10 may be a general consent that is to be used by the pharmacy 14 for this and future medical items. It is also possible that the consent could be limited in some way, such as for certain items or classes of items but not for others.

Figure 3:
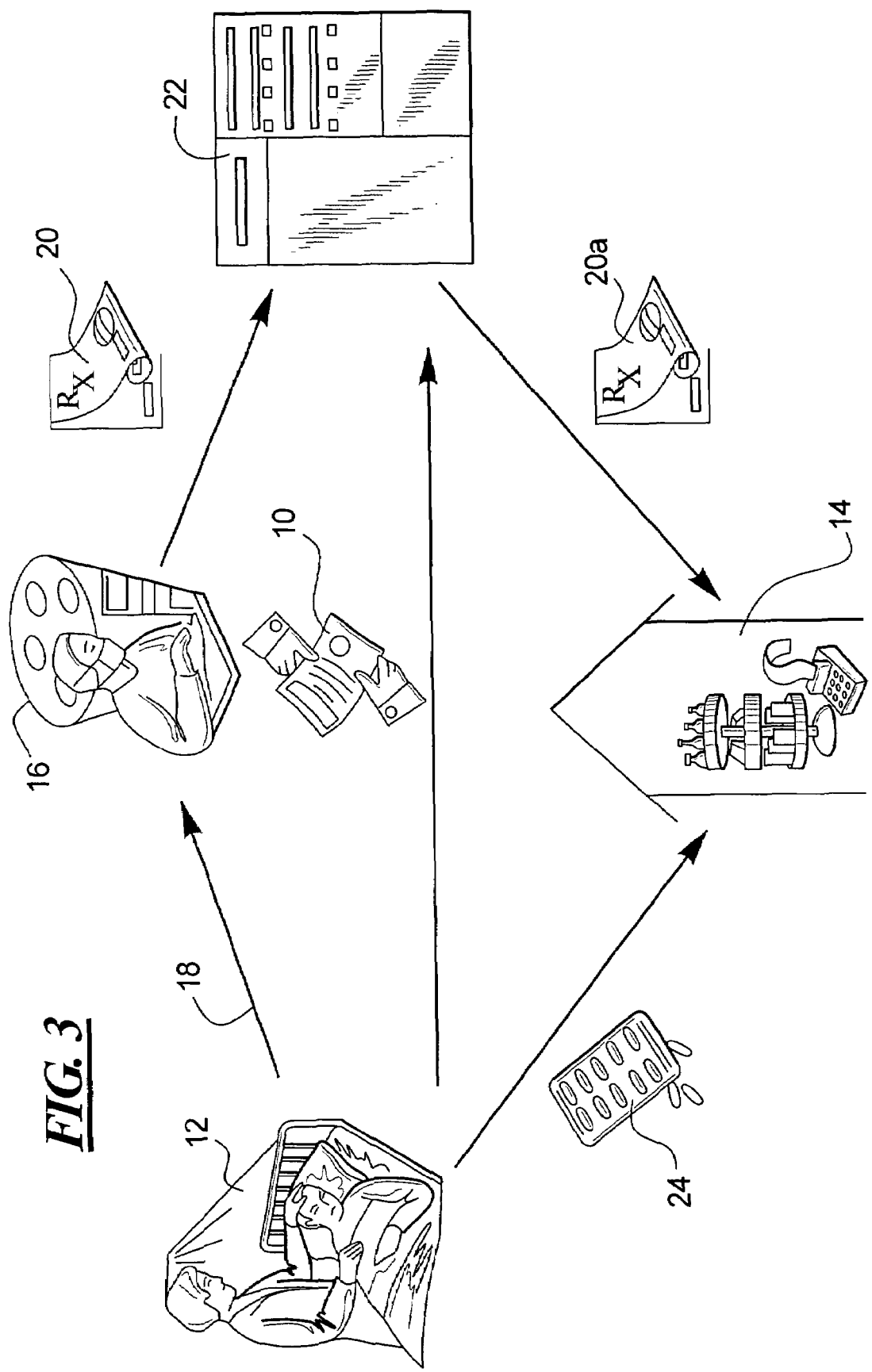
FIG. 3 is a schematic diagram of a third embodiment of the method and system.

In another variation as shown in FIG. 3, referred to here as the "push" variation, a statement 10 is provided by the patient 12 to the server 22 where the statement, or consent, 10 is stored. The patient 12 is seen by a medical professional 16 as indicated at 18, who prepares an e-prescription 20 that is then forwarded to the server 22. Since the consent statement 10 is provided first before the patient has a prescription, this variation is referred to as the general consent variation. The server 22 assigns each e-prescription 20 that matches to a patient 12 as identified by a consent statement 10 to the pharmacy 14 that is identified in the consent statement 10. The server 22 transforms the e-prescription into orders 20a for the prescribed medical item that are sent to the corresponding pharmacy 14 on behalf of the respective patient 12. The orders 20a may be forwarded from the server 22 to the pharmacy 14 immediately upon receipt of the prescription 20 by the server (or reasonably soon thereafter), or at a given time, or at regular intervals, or upon the occurrence of regular events.

In this "push" variation, the pharmacy 14 must be able to receive the orders 20a, and to fill the prescription 20. Filling of the prescription may include delivery of the medical item 24 to the patient 12. The pharmacy 14 should also be able to bill for the prescribed medical items. The patient 12 mentioned in the consent statement 10 and to whom the medical items are provided may not be person or entity being billed for the medical items. In such cases, the consent statement 10 preferably identifies not only the patient to receive the medical items 24 but also identifies the entity to be billed for the medical items.

Trust is established in this "push" variation for security reasons. In particular, the patient 12 must have reason to believe that the server 22 will forward the e-prescriptions to the pharmacy or agent 14. The patient 12 is counting on having fast and correct delivery and billing for the medical items. The server 22 has to trust that the patient is the correct recipient of the medical items 24 and that someone will pay for them. The pharmacy or agent 14 has to know that the server 22 is entitled to manage and forward the e-prescriptions, and the server 22 must trust that the pharmacy 14 will quickly and honestly send the correct medical items to the proper patient 12 as ordered by the server 22.

Figure 4:
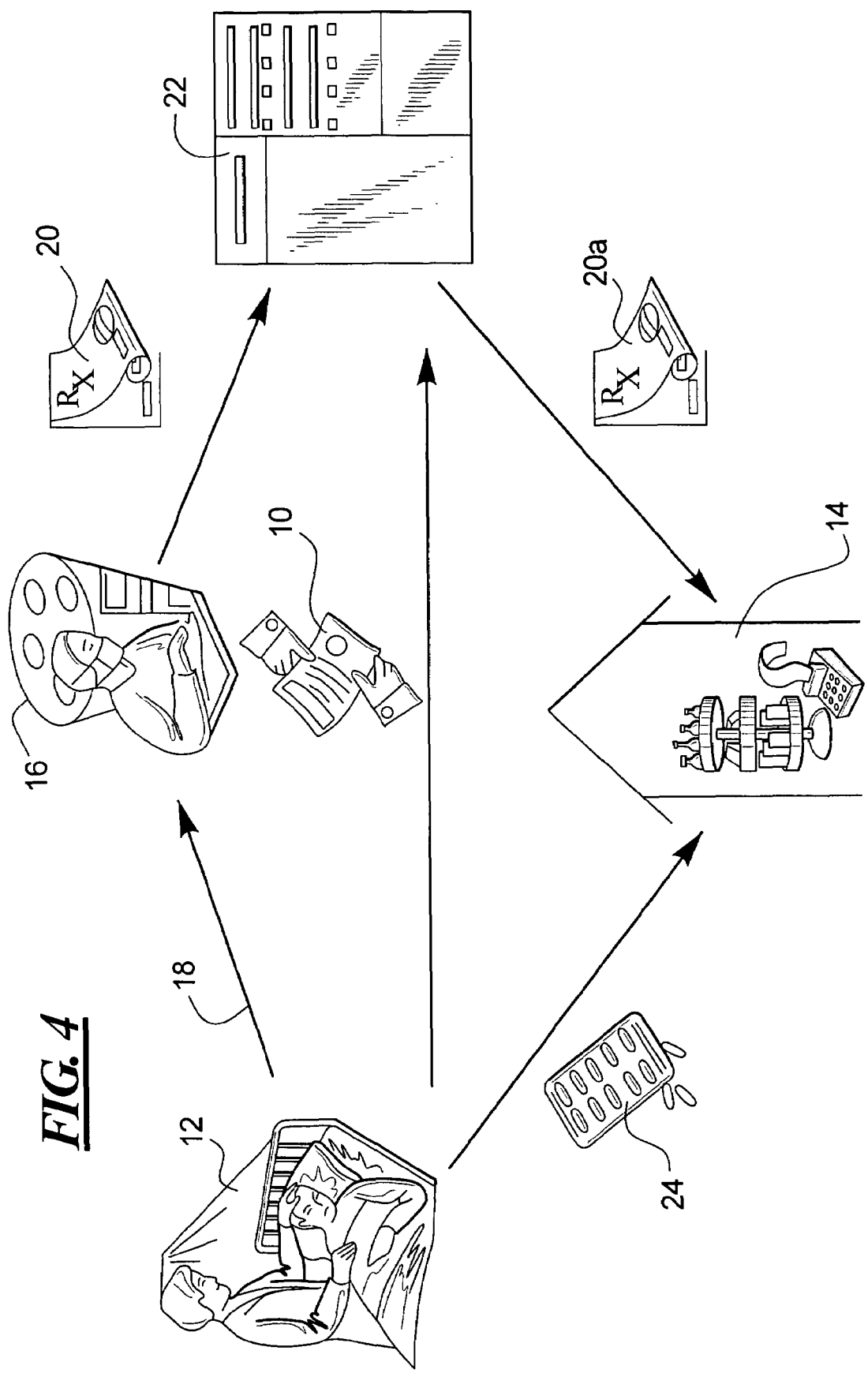
FIG. 4 is a schematic diagram of a fourth embodiment of the method and system.

Referring now to FIG. 4, the "push" variation may also be configured in a per-case consent variation. The per-case variation provides that the patient 12 first sees the medical professional 16 as indicated at 18. The medical professional 16 prepares an e-prescription 20 that is sent to the server 22. The patient 12 then prepares a consent statement 10 that is sent by the patient to the server 22. The server 22 issues an order 20a for the prescribed items to the pharmacy or agent 14. The pharmacy or agent 14 fills the prescription and provides the medical items 24 to the patient 12.

In an alternative, the agent that is mentioned in the consent statement 10 is not the pharmacy or agent 14 that is identified at the time the consent statement 10 was written. Instead, the agent is a set of rules that is used to determine the agent or pharmacy. The agent could also be an agent that is identified as the person or entity that determines the pharmacy 14 to which the prescription order 20*a* is to be sent. This may be on a per prescription basis, for example, at a later time such as when an e-prescription is available and active.

In the present invention, the billing portion of the process includes the financial transaction for parts of the medical items prescribed transaction or the financial transaction for the entirety of the items prescribed. For example, some of the items may be provided by one entity and others provided by one or more other entities.

Another aspect of the present invention is that the patient 12 mentioned in the consent statement 10 is not the author of the consent statement 10 but merely the beneficiary of the prescription. This may be the case were the patient is underage and the consent statement is provided by the parent or guardian, or for those patients for whom a custodian has been appointed. Other situations involving patients who are unable to provide informed consent, such as those afflicted with dementia or patients in a coma, may require a guardian and are also within the scope of this invention.

The consent statement may be prepared in the office of a general practitioner doctor (GP) or other medical professional. In one embodiment, the consent statement is prepared and forwarded using software at the doctor's office for such purpose. The consent statement may instead be prepared at a pharmacy using software at the pharmacy, or may be prepared at a hospital or other medical facility using, for example, the hospital information system (HIS). The consent statement may be prepared via an Internet browser accessing a web portal of the e-prescription server or other Internet site. The forms or software for preparing the consent statement may be provided to the patient, at home, at a care facility or nursing home, or other place. Other means for preparing the consent statement may also be provided, within the scope of the present invention.

The selection of a pharmacy or agent 14 may be step in the present method. The pharmacy or agent 14 may be selected using a search engine or brokerage engine. The search may be used as part of the preparation of the consent statement. Factors in deciding on a pharmacy or agent 14, whether decided by the patient or used by the search engine, include: availability of the medical items identified in the prescription, cost, geographic distance, type/size/weight/other properties of the medical item to be delivered. Other selection criteria may be used as well.

An advantage provided by the present invention is in allowing the pharmacy to dispense the medical items immediately upon issuance of the e-prescription, which is sent to the agent electronically when issued. The medical items are available to the patient in a shorter time, which likely increases the patient's comfort. The prompt dispensing of the medical items tightens the link to the patient identity and the decreases the likelihood of fraud with respect to the patient identity.

Thus, there has been shown and described a method and system for dispensing medical items via electronic prescriptions. Variations of the present method include a pull variation and a push variation, each of which has a variation for a general consent statement and for a per-case consent statement. The present method and system includes a server for handling e-prescriptions. Consent statements by the patient are provided either to the server or to the pharmacy. Communications are carried out between the people and entities preferably using secure communications to establish trust where needed.

Although other modifications and changes may be suggested by those skilled in the art, it is the intention of the inventors to embody within the patent warranted hereon all changes and modifications as reasonably and properly come within the scope of their contribution to the art.

We claim:

1. A method for providing medical items to a patient, comprising the steps of:

receiving an encrypted message on a computer system at an intermediary agent from a trusted sender, the encrypted message containing a consent statement from the patient, the consent statement providing permission of the patient for the intermediary agent to receive a prescription prepared for the patient by a medical professional and providing permission of the patient for the intermediary agent to transmit the prescription to a pharmacy service, said consent statement being one of two types, wherein a first type of consent statement is a general consent statement granting permission by the patient to fill a plurality of prescriptions and a second type of consent statement being a per-case consent statement granting permission by the patient to file a predetermined prescription;

receiving an encrypted message on a computer system at the intermediary agent from a trusted sender, the encrypted message containing an electronic prescription prepared for the patient by a medical professional;

storing the electronic prescription on a server; and transmitting an encrypted message containing the electronic prescription to a trusted receiver via the computer system from the intermediary service, the trusted receiver being a pharmacy service for filling of the prescription as authorized by the consent statement if the consent statement is a general consent statement, otherwise receiving a confirmation from the patient of instructions to transmit an encrypted message containing the electronic prescription to the pharmacy service as a trusted receiver if the consent statement is a per-case consent statement, and transmitting an encrypted message containing the electronic prescription to the pharmacy service as a trusted receiver.

2. A method for providing medical items to a patient, comprising the steps of:

receiving an encrypted message from a trusted sender on a computer system at a pharmacy service, the encrypted message containing a consent statement from the patient, the consent statement providing permission of the patient for the pharmacy service to receive a prescription prepared for the patient by a medical professional and providing permission of the patient for the pharmacy service to fill the prescription, said consent statement being one of two types, wherein a first type of consent statement is a general consent statement granting permission by the patient to fill a plurality of prescriptions and a second type of consent statement being a per-case consent statement granting permission by the patient to file a predetermined prescription;

receiving an encrypted message from a trusted sender on the computer system at the pharmacy service, the encrypted message containing an electronic prescription prepared for the patient by a medical professional;

storing the consent statement on a server of the pharmacy service;

storing the electronic prescription on the server of the pharmacy service;

for a general consent statement, providing the medical item identified in the prescription to the patient;

for a per-case consent statement, receiving a confirmation from the patient of instructions to transmit the electronic prescription to the pharmacy service if the consent statement is a per-case consent statement, and transmitting the electronic prescription to the pharmacy service;

wherein said consent statement is provided by the patient to the pharmacy service authorizing the pharmacy service to act as an agent for the patient for purposes of receiving and filling the prescription.

3. A method as claimed in claim 1, wherein said step of receiving the encrypted message containing the electronic prescription includes receiving the electronic prescription at a server.

4. A method as claimed in claim 3, wherein said intermediary agent is a server acting as an agent of the patient for purposes of receiving the prescription and transmitting the prescription to a pharmacy to be filled.

5. A method for providing medical items to a patient, comprising the steps of:

establishing a first communication connection with a patient via a computer network;

establishing the identity of the patient via communications over said first communication connection;

receiving a secure communication from the patient via the first communication connection;

accessing contents of the secure communication from the patient, said secure communication including a consent statement of the patient for a pharmacy service to receive a prescription prepared for the patient by a medical professional and for the pharmacy service to fill the prescription with a medical item, said consent statement also providing consent to the pharmacy service to provide the medical item of the prescription to an authorized agent of the patient;

storing the consent statement on a server of the computer network;

establishing a second communication connection to a medical professional via the computer network;

establishing the identity of the medical professional via communications over said second communications connection;

receiving a secure communication from the medical professional via the second communication connection;

accessing contents of the secure communication from the medical professional, said secure communication including a prescription for a medical item for the patient;

storing the prescription on a server of the computer network;

notifying at least one of the patient and the authorized agent that the prescription has been received;

receiving contact from the authorized agent at the service;

establishing a verified identify of the authorized agent; and providing the medical item of the prescription to the authorized agent for transport to the patient.

\* \* \* \* \*